(12) United States Patent
Anderson

(10) Patent No.: US 7,508,195 B2
(45) Date of Patent: Mar. 24, 2009

(54) ANTI-DISTORTION ELECTROMAGNETIC SENSOR METHOD AND SYSTEM

(75) Inventor: Peter Traneus Anderson, Andover, MA (US)

(73) Assignee: General Electric Company, Schenectady, NY (US)

( * ) Notice: Subject to any disclaimer, the term of this patent is extended or adjusted under 35 U.S.C. 154(b) by 19 days.

(21) Appl. No.: 11/654,878

(22) Filed: Jan. 18, 2007

(65) Prior Publication Data

US 2008/0174303 A1 Jul. 24, 2008

(51) Int. Cl.
*H01F 27/28* (2006.01)
*H01F 5/00* (2006.01)
*G01B 7/14* (2006.01)

(52) U.S. Cl. .......................... 324/207.16; 324/207.17; 336/232; 335/299

(58) Field of Classification Search ............ 324/207.15, 324/207.16, 207.17, 207.23, 207.26, 247; 336/200, 232; 343/895, 824; 600/424
See application file for complete search history.

(56) References Cited

U.S. PATENT DOCUMENTS

| 1,450,080 | A | | 3/1923 | Hazeltine | |
|---|---|---|---|---|---|
| 4,710,708 | A | | 12/1987 | Rorden | |
| 4,849,692 | A | | 7/1989 | Blood | |
| 4,945,305 | A | | 7/1990 | Blood | |
| 5,425,382 | A | | 6/1995 | Golden | |
| 5,453,686 | A | * | 9/1995 | Anderson | 324/207.17 |
| 5,558,091 | A | | 9/1996 | Acker | |
| 5,592,939 | A | | 1/1997 | Martinelli | |
| 5,640,170 | A | * | 6/1997 | Anderson | 343/895 |
| 5,676,673 | A | | 10/1997 | Ferre | |
| 5,747,996 | A | | 5/1998 | Fuchs | |
| 5,782,765 | A | | 7/1998 | Jonkman | |
| 5,800,352 | A | | 9/1998 | Ferre | |
| 5,803,089 | A | | 9/1998 | Ferre | |
| 5,829,444 | A | | 11/1998 | Ferre | |
| 5,873,822 | A | | 2/1999 | Ferre | |
| 5,913,820 | A | | 6/1999 | Bladen | |
| 5,967,980 | A | | 10/1999 | Ferre | |
| 6,052,610 | A | | 4/2000 | Koch | |
| 6,073,043 | A | | 6/2000 | Schneider | |
| 6,129,668 | A | | 10/2000 | Haynor | |

(Continued)

FOREIGN PATENT DOCUMENTS

WO WO9736192 10/1997

OTHER PUBLICATIONS

Takaaki Nara, et al.; "A Closed-Form Formula for Magnetic Dipole Localization by Measurement of Its Magnetic Field and Spatial Gradients"; Digital Object Identifier; 2006 IEEE; pp. 3291-3293.

*Primary Examiner*—Kenneth J Whittington
(74) *Attorney, Agent, or Firm*—Fletcher Yoder

(57) ABSTRACT

A source for inducing an electromagnetic magnetic field, comprising: a substrate, a conductive layer coupled to the substrate, and a planar coil coupled to the substrate, wherein the planar coil comprises non-concentric rings, and wherein the non-concentric rings are configured such that a drive current applied across the non-concentric rings provides a magnetic field, and wherein the magnetic field comprises a moment vector that is tilted at an angle from the normal to a plane of the planar coil. Also provided are a method of electromagnetic tracking, a method of manufacture of a planar coil, and an electromagnetic sensor.

26 Claims, 10 Drawing Sheets

U.S. PATENT DOCUMENTS

| | | |
|---|---|---|
| 6,172,499 B1 | 1/2001 | Ashe |
| 6,175,756 B1 | 1/2001 | Ferre |
| 6,201,387 B1 | 3/2001 | Govari |
| 6,226,547 B1 | 5/2001 | Lockhart |
| 6,246,231 B1 | 6/2001 | Ashe |
| 6,374,134 B1 | 4/2002 | Bladen |
| 6,445,943 B1 | 9/2002 | Ferre |
| 6,502,031 B2 | 12/2002 | Uehara |
| 6,539,327 B1 | 5/2003 | Dassot |
| 6,701,179 B1 | 3/2004 | Martinelli |
| 6,774,624 B2 | 8/2004 | Anderson |
| 6,862,004 B2 * | 3/2005 | Alexopoulos et al. ....... 343/895 |
| 6,980,921 B2 | 12/2005 | Anderson |
| 7,015,859 B2 | 3/2006 | Anderson |
| 7,096,148 B2 | 8/2006 | Anderson |
| 7,158,754 B2 | 1/2007 | Anderson |
| 2001/0045826 A1 * | 11/2001 | Schneider ............. 324/207.17 |
| 2005/0235482 A1 * | 10/2005 | Deaett et al. .................. 29/600 |
| 2006/0058604 A1 | 3/2006 | Avinash |
| 2006/0106292 A1 | 5/2006 | Anderson |
| 2006/0247511 A1 | 11/2006 | Anderson |

* cited by examiner

ANTI-DISTORTION ELECTROMAGNETIC SENSOR METHOD AND SYSTEM

BACKGROUND

This disclosure relates generally to tracking systems that use magnetic fields to determine positions and orientations of an object, such as systems used for tracking instruments and devices during surgical interventions and other medical procedures. More particularly, this disclosure relates to a system and method for reducing magnetic field distortion in such systems.

Tracking systems have been used in various industries and applications to provide position information relating to objects. For example, electromagnetic tracking may be useful in aviation applications, motion sensing applications, and medical applications. In medical applications, tracking systems have been used to provide an operator (e.g., a physician) with information to assist in the precise and rapid positioning of a medical device located in or near a patient's body. In general, an image may be displayed on a monitor to provide positioning information to an operator. The image may include a visualization of the patient's anatomy with an icon on the image representing the device. As the device is positioned with respect to the patient's body, the displayed image is updated to reflect the correct device coordinates. The base image of the patient's anatomy may be generated either prior to, or during, the medical procedure. For example, any suitable medical imaging technique, such as X-ray, computed tomography (CT), magnetic resonance imaging (MRI), positron emission tomography (PET), and ultrasound, may be utilized to provide the base image displayed during tracking. The combination of the base image and the representation of the tracked device provides positioning information that allows a medical practitioner to manipulate a device to a desired position and/or associate information gathered to a precise location.

To determine device location, tracking systems may utilize a method of electromagnetic (EM) field generation and detection. Using this method, at least one magnetic field is generated from one or more EM sensors, and the magnetic fields are detected by one or more complementary EM sensors. In such a system the mutual inductance of the EM field detected may be processed to resolve a position and/or orientation of the EM sensors relative to one another. For example, an EM sensor may be fixed in a known position, with a complementary EM sensor mounted at the operative end of a device. While the EM sensor generates a magnetic field, the magnetic field characteristics may be detected by the complementary EM sensor. The detected characteristics may be processed to determine the position and orientation (e.g., the X, Y and Z coordinates, as well as the roll, pitch and yaw angles) of the EM sensors relative to one another.

However, as will be appreciated, the presence of field distorting objects in or near the magnetic field may cause distortions of the magnetic field emitted from the EM sensors. As a result, the magnitude and direction of the magnetic field sensed by the complementary EM sensor may be inaccurate. Distortions, such as these, may come from a multitude of sources, including: signals from other electromagnetic sources, the magnetic fields generated by eddy currents in another conductive object, and the field distorting effect of a ferro-magnetic objects. Unless compensated for, or significantly reduced, these distortions and inaccuracies may produce an error in the determined location of the device. For example, a source of magnetic field distortion may include the equipment surrounding the tracking system (e.g., a metal surgery table or conductive medical devices). In these instances, the electromagnetic field generated by the EM sensors may induce eddy currents into a metal surface. The eddy currents may produce additional electromagnetic fields that distort the electromagnetic field originally generated by the EM sensor, thereby creating errors in the determined position and orientation of the complementary EM sensor. Although, methods are known to map and compensate for the distortions, if the distortions become too significant, mapping may not be capable of compensating for the distortions.

Accordingly, there is a desire to provide an electromagnetic field tracking system where the effects of electromagnetic field distorters is reduced and/or eliminated.

BRIEF DESCRIPTION

In accordance with one aspect, provided is a source for inducing an electromagnetic magnetic field, comprising: a substrate; a conductive layer coupled to the substrate; and a planar coil coupled to the substrate, wherein the planar coil comprises non-concentric rings, wherein the non-concentric rings are configured such that a drive current applied across the non-concentric rings provides a magnetic field, and wherein the magnetic field comprises a moment vector that is tilted at an angle from the normal to a plane of the planar coil.

In accordance with another aspect, provided is a method of electromagnetic tracking, comprising: inducing a drive current into a planar coil located on one side of an electrically conductive layer, wherein the planar coil comprises non-concentric rings, and wherein the non-concentric rings are configured such that inducing the drive current across the planar coil provides a magnetic field, wherein the magnetic field comprises a moment vector that is tilted at an angle from the normal to a plane of the planar coil.

In accordance with yet another aspect, provided is a method of manufacture of a planar coil, comprising: coupling a planar coil to an electrically conductive layer, wherein the planar coil comprises non-concentric rings, and wherein the non-concentric rings are configured such that a inducing drive current across the planar coil provides a magnetic field, wherein the magnetic field comprises a moment vector that is tilted at an angle from the normal to a plane of the planar coil.

In accordance with yet another aspect, provided is an electromagnetic sensor, comprising: an insulating layer having a first surface and a second surface, the second surface being opposite the first surface; a conductive layer coupled to the second surface of the insulating layer; and a planar coil coupled to the first surface of the insulating layer, wherein the planar coil comprises non-concentric rings, wherein the non-concentric rings are configured such that a drive current applied across the non-concentric rings provides a magnetic field, and wherein the magnetic field comprises a moment vector that is tilted at an angle from the normal to a plane of the planar coil.

DRAWINGS

These and other features, aspects, and advantages will become better understood when the following detailed description is read with reference to the accompanying drawings in which like characters represent like parts throughout the drawings, wherein.

DETAILED DESCRIPTION

Figure 1:
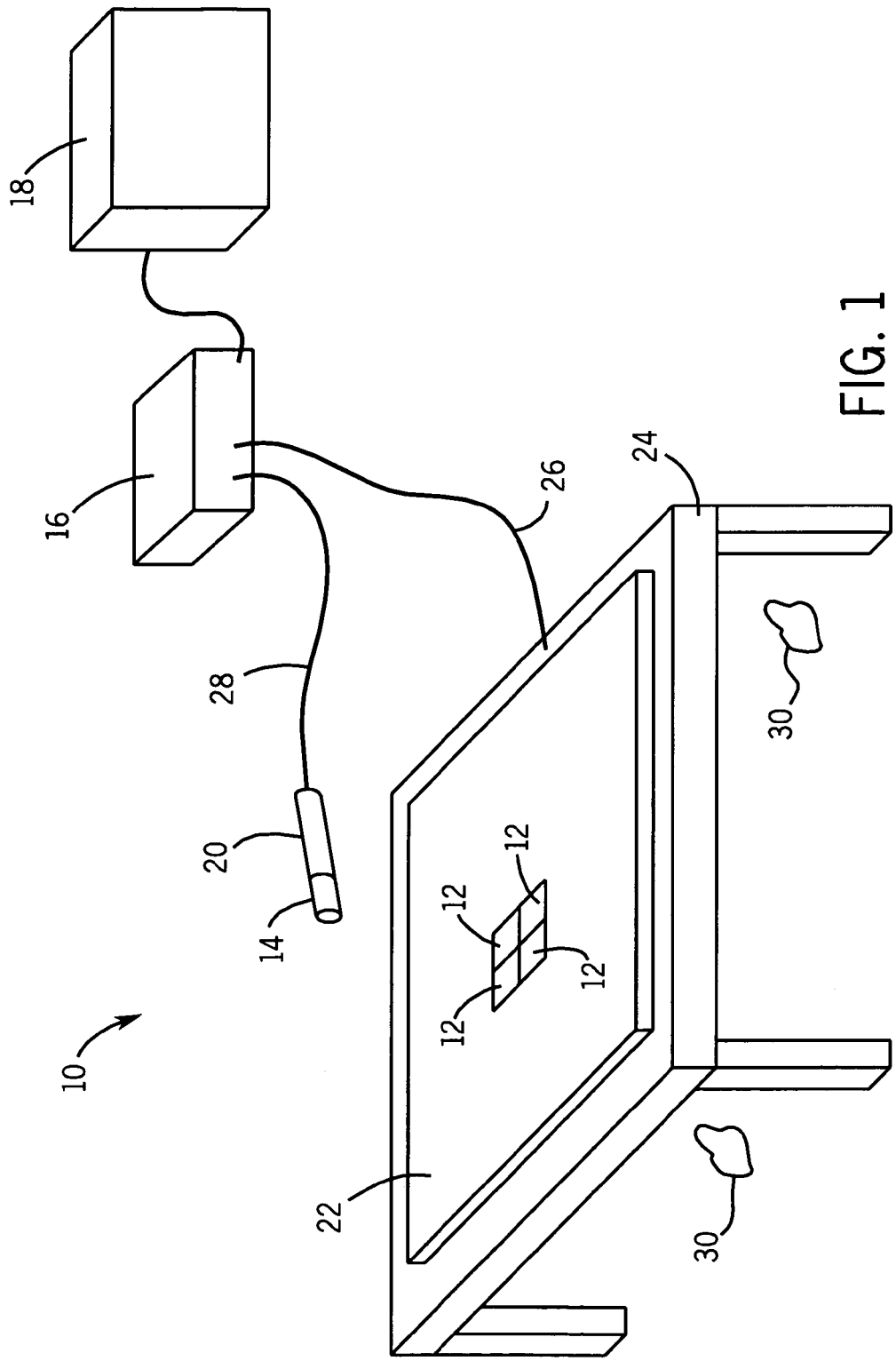
FIG. 1 is an illustration of an exemplary system for magnetic field tracking implementing certain aspects of the present technique.

Referring now to FIG. 1, a tracking system 10 in accordance with one embodiment of the present technique is illustrated. The tracking system 10 may generally include multiple tracking components. As depicted, the tracking components may include a plurality of electromagnetic (EM) sensors 12, at least one complementary EM sensor 14, a processor 16 and a user interface 18. The at least one complementary EM sensor 14 may be coupled to at least one instrument 20.

Generally, the EM sensors 12 may be formed from magnetic dipoles (e.g., coils, current loops, or electromagnets) capable of producing a dipole magnetic field when a current is applied across them. As illustrated, the EM sensors may be coupled to a conductive layer 22 that is disposed on table 24. By way of example, the conductive layer 22 may be located between the EM sensors 12 and the table 24. In some embodiments, the EM sensors 12 may employ industry-standard coil architecture ("ISCA"), a single dipole coil, a planar coil, or a combination of the three. ISCA is defined as three approximately collocated, approximately orthogonal, and approximately dipole coils. EM sensors 12 configured with a single coil may generate a single dipole magnetic field, while EM sensors 12 configured with multiple coils may be capable of providing multiple dipole magnetic fields of varying magnitude and direction. By way of example, the EM sensors 12 may be implemented wherein each of the EM sensors 12 includes three orthogonal magnetic dipoles and thus generates a dipole magnetic field in three planes (i.e., X, Y and Z planes).

The magnetic field generated by each of the EM sensors 12 may be dependent upon a current that is provided across the coil of the respective sensor. In one embodiment, to provide a current across the coil, the processor 16 may provide a drive current to each of the EM sensors 12, via cable 26, as illustrated in FIG. 1. As will be appreciated, while EM sensors 12 are depicted as wired, EM sensors 12 may be wired or wireless. With the current flowing across the coils of the EM sensors 12, the EM sensors 12 may generate at least one dipole magnetic field with a given magnitude and direction. Characteristics of the magnetic field (e.g., magnitude, direction, phase or frequency) may be varied by manipulating the current.

In the depicted system 10, the at least one complementary EM sensor 14 may be configured to sense the magnetic field generated by each of the EM sensors 12. For example, sensing the magnetic field may include the at least one complementary EM sensor 14 sensing the mutual inductance of the magnetic field. Similar to the EM sensors 12, embodiments of the at least one complementary EM sensor 14 may include an ISCA, a single dipole coil, a planar coil, or a combination of the three. The coils of the at least one complementary EM sensor 14 are configured for sensing the magnetic field generated by the EM sensors 12. As will be appreciated, the mutual inductance of EM sensors 12 and the at least one complementary EM sensor 14 are the same, regardless as to which sensors generate the EM field. Therefore, positioning and functionality of the at least one complementary EM sensor 14 and EM sensor 12 in the system 10 may be reversed. For example, in one embodiment, the at least one complementary EM sensor 14 may generate the EM field, while the EM sensors 12 may be configured to sense the magnetic field. For simplicity, the remainder of this paper may refer to the EM sensors 12 as generating a magnetic field, while the at least one complementary EM sensor 14 may be configured to sense the magnetic field.

In either of these configurations, the data gathered by the at least one complementary EM sensor 14 may be processed to determine various parameters. For example, in the illustrated embodiment of FIG. 1, the magnetic field sensed from the at least one complementary EM sensor 14 may be output to a processor 16, via a cable 28. As will be appreciated, while the at least one complementary EM sensor 14 is depicted as wired, the at least one complementary EM sensor 14 may be wired or wireless. In another embodiment, the processor 16 may monitor the magnetic field sensed by the at least one complementary EM sensor 14 to determine a location (e.g., position and/or orientation) of each complementary EM sensor 14 with respect to the EM sensors 12.

As mentioned previously, the at least one complementary EM sensor 14 and/or EM sensors 12 may be configured as having multiple coils. For example, each of the EM sensors 12 may include three concentric orthogonal dipole coils (coil trios). As will be appreciated, in such an embodiment, a current may be induced across all three coils of the coil trio to simultaneously generate three magnetic fields from one of the EM sensors 12. The magnetic field generated by each respective coil may be distinguished by varying phase and frequency of each magnetic fields generated. The at least one complementary EM sensor 14 may then sense each of three magnetic fields generated, and transmit the data received to the processor 16. The processor 16 may distinguish each of the magnetic fields by identifying the respective phase and frequency. As will be appreciated, depending on the number of magnetic fields generated and received, multiple degrees of freedom may be resolved by the processor 16. For example, wherein an EM sensor 12 and complementary EM sensor 14 each include a coil trio, six degrees of freedom, including three position values and three orientation values may be determined (i.e., X, Y, Z and roll, pitch, yaw).

As illustrated by FIG. 1, the at least one complementary EM sensor 14 may be coupled to at least one instrument 20. In medical tracking applications, the at least one instrument 20 may include devices used during a medical procedure. As will be appreciated by a person of ordinary skill in the art, the present technique may be used to track a variety of instruments 16 used during medical procedures. For example, the at least one instrument 20 may be a drill, a guide wire, a catheter, an endoscope, a laparoscope, a biopsy needle, an ablation device or other medical devices.

In general, the processor 16 may perform several functions in the tracking system 10. For example, the processor 16 may include electronic circuitry to provide the drive signals, electronic circuitry to receive the sensed signals, and electronic circuitry to condition the drive signals and the sensed signals. Further, the processor 16 may include processing to coordinate functions of the system 10, to implement navigation and visualization algorithms suitable for tracking and displaying the position and orientation of an instrument or device on a monitor. The processor may include a digital signal processor, memory, a central processing unit (CPU) or the like, for processing the acquired signals. As will be appreciated, the processing may include the use of one or more computers within the processor 16. The addition of a separate CPU may provide additional functions for tracking, including, but not limited to, signal processing of data received, and transmission of data to the user interface 18, including a display. In one embodiment, the CPU may be confined within the processor 16, while in another embodiment a CPU may include a stand-alone device that is separate from the processor 16.

As mentioned, system 10 may also include a user interface 18. For example, the system 10 may include a monitor configured to display the position and orientation of the at least one instrument 20 or device. Thus, a medical practitioner may monitor the position of the at least one instrument 20 or device on the user interface 18. As will be appreciated, the user interface 18 may also include additional devices to facilitate the exchange of data between the system 10 and the user. For example, the user interface 18 may include a keyboard, mouse, printers or other peripherals. While the processor 16 and the user interface 18 may be separate devices, in certain embodiments, the processor 16 and the user interface 18 may be provided as a single unit.

As will be appreciated, in the embodiment depicted in FIG. 1, the magnetic field may be susceptible to interference from distorting objects (e.g., conductive objects 28) located within the vicinity of the generated magnetic field. For example, if the EM sensors 12 are placed on top of a metal surgery table 24 (see FIG. 1), the magnetic field may be susceptible to interference from eddy currents generated on the surface of the metal table 24, and other distorting objects 30 located above and below the plane of the EM sensors 12. It is desirable for EM sensors 12 to be designed and implemented in such a manner as to eliminate or reduce the distortion caused by distorting objects, such as distorting objects 30 and table 24. In accordance with some aspects of the present technique, a planar coil formed from non-concentric rings, provides for tilting the moment vector of a single magnetic field. Further, in accordance with some aspects of the present technique, a conductive layer 22 is provided to shield the magnetic field from distortions in at least one direction. Additional aspects of the present technique provide for a conductive layer 22 that shields multiple planar coils in one direction, while allowing the combination of the tilted moment vectors of each coil to provide three generally orthogonal magnetic fields for use in tracking applications.

Figure 2:
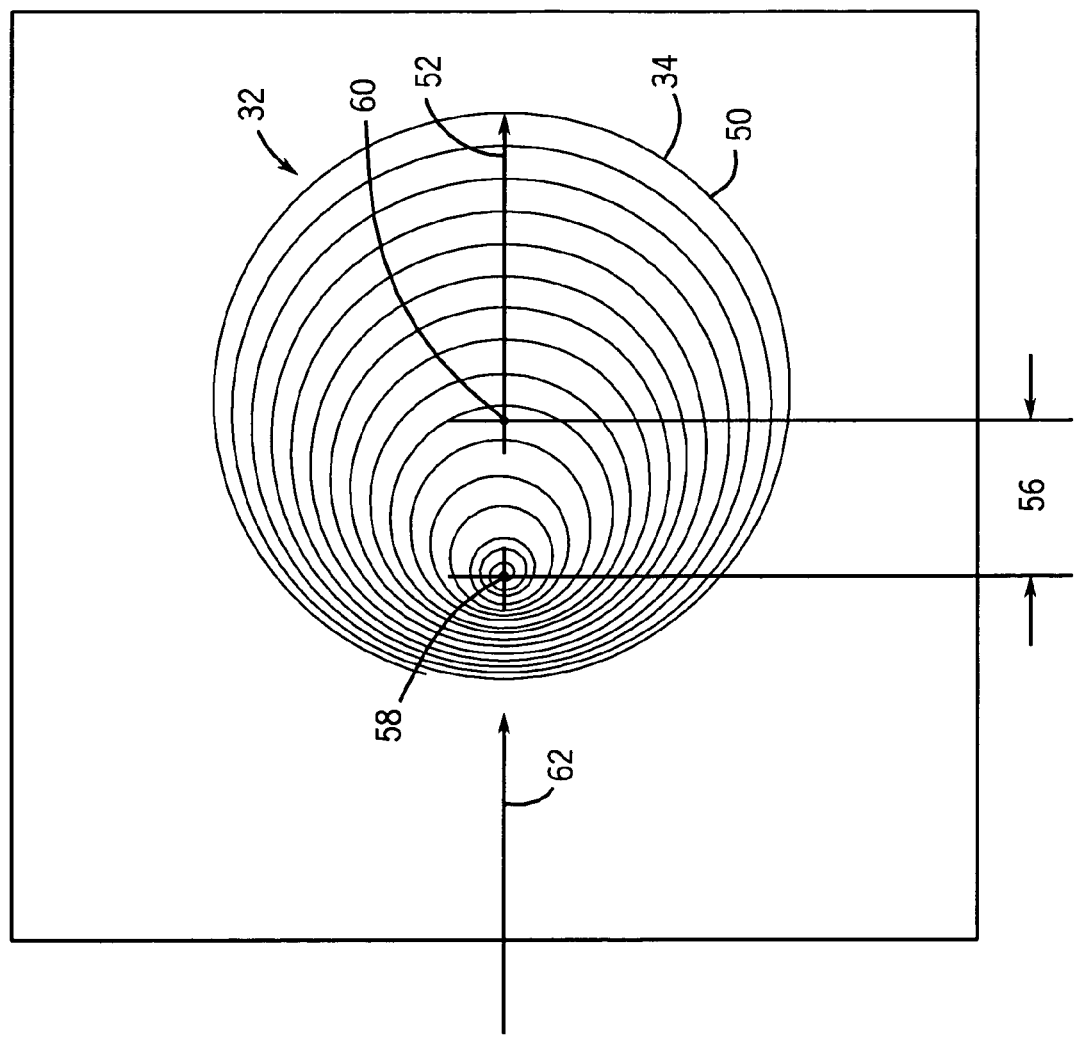
FIG. 2 is an illustration of an exemplary planar coil in accordance with certain aspects of the present technique.
Figure 3:
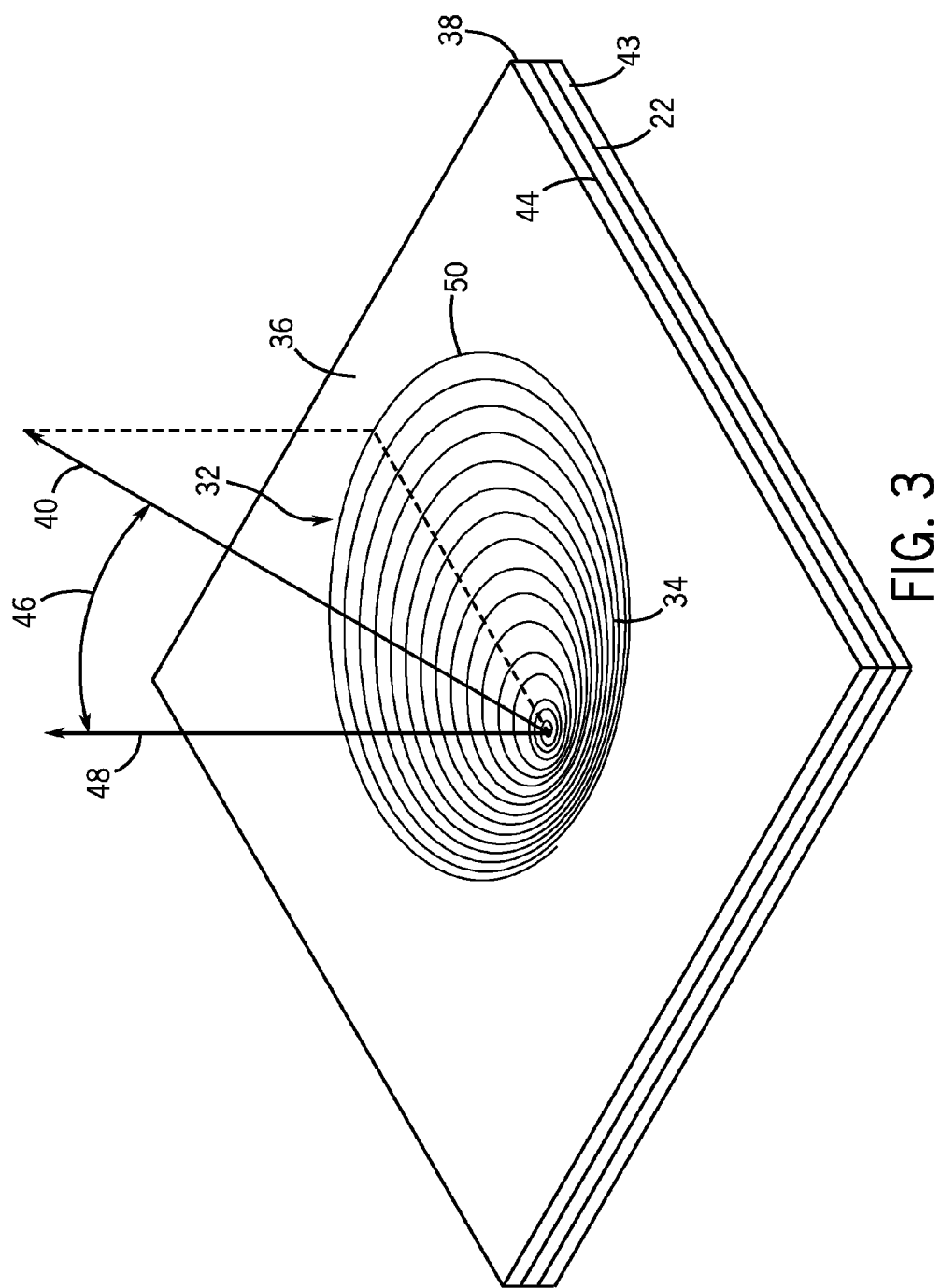
FIG. 3 is an illustration of an exemplary planar coil and a tilted dipole moment vector generated by the planar coil in accordance with certain aspects of the present technique.

Turning now to FIGS. 2 and 3, a non-concentric planar coil 32 is depicted in accordance with aspects of the present technique. The embodiment of FIGS. 2 and 3 depict a non-concentric planar coil 32 that includes non-concentric rings 34. Generally, the non-concentric rings 34 may be formed from a conductive material disposed upon a top surface 36 of an insulating layer 38 that is planar in shape. In the illustrated embodiment, for example, the non-concentric planar coil 32 may be formed from at least one copper trace disposed as a spiral approximating a plurality of non-concentric rings 34 on the surface of a printed circuit board (PCB). In one embodiment, the spiral trace forming the non-concentric rings may be approximately 0.005 inches wide and 0.0005 inches thick and 0.005 inches or more apart.

To generate a magnetic field, a current may be induced across the non-concentric rings 34 of the non-concentric planar coil 32. As will be appreciated, the current induced across the non-concentric planar coil 32 may create a dipole magnetic field with a moment vector 40 in a direction normal or perpendicular to the non-concentric planar coil 32. As depicted in FIGS. 2 and 3, there is a conductive layer 22 and possibly an additional ferromagnetic layer 43 located on a bottom surface 44 of the insulating layer 38 opposite the top surface 36 having the non-concentric planar coil 32 formed thereon. Accordingly, the magnetic field, created by inducing a current across the non-concentric planar coil 32, may not extend below the non-concentric planar coil 32 and the insulating layer 38.

In one embodiment, the non-concentric planar coil 32 may be configured to provide for tilting of the magnetic field moment vector 40 at a tilt angle 46 from the normal vector 48. For example, as illustrated, the non-concentric planar coil 32 may include a single spiral approximating a plurality of non-concentric rings 34. The location of the non-concentric rings 34 of FIGS. 2 and 3 may be derived by shifting each of the non-concentric rings 34, from a concentric position, in a single direction (shown by arrow 62) at a distance proportional to the radius of each respective ring 34. For example, as depicted in FIGS. 2 and 3, the outer ring 50 of non-concentric planar coil 32 may have been shifted at a distance 56 (from origin 58 to the shifted center 60) that is proportional to the radius 52 of the ring 50. Similarly, each of the non-concentric rings 34 in the planar coil 32 may be shifted from the origin 58 in the direction 62 at a distance from the origin 58 to a shifted center, wherein the distance is proportional to the radius of each respective ring. As will be appreciated by those of ordinary skill in the art, the shift distance may be affected by several factors, including but not limited to the desired tilt angle (discussed below), the thickness of the rings, and the original distance between each ring. These considerations may optimize performance and prevent the non-concentric rings 34 from contacting one another, and thereby destroying the conductive path through the entire coil.

As discussed previously, embodiments of the planar coil 32 may provide for tilting of the moment vector 40 from the normal vector 48 of the non-concentric planar coil 32. As will be appreciated, where the non-concentric rings 34 of the planar coil 32 are positioned as those depicted in FIG. 3, the current density in non-concentric rings 34 may vary inversely with the square of the ring radius 52. In light of this consideration, where the center 60 of each of the non-concentric rings 34 is displaced from the origin 58 by a distance 56 proportional to the radius 52 of each of the non-concentric rings 34, the tilt angle 46 ($\theta$) is derived from:

$$\mathrm{Tan}(\theta) = (\text{shift of ring})/(\text{radius of ring})$$

The "shift of ring" is represented by the distance 56 from the origin 58 to the shifted center 60 of each of the respective non-concentric rings 34. The "radius of ring" corresponds to the respective radius 52 of each of the non-concentric ring 34 in the shift direction 62. For example, the tilt angle 46 for the outer ring 50 may be derived from the arctangent of the distance 56 divided by the radius 52 of the outer ring 50. The tilt angle 46 represents the angle of the moment vector 40 from the normal vector 48 to the non-concentric planar coil 32. In one embodiment, to avoid two non-concentric rings 34 intersecting as a result of the shifted position, the tilt angle 46 is limited to less than the arctangent of the square root of 2 or approximately 45 degrees. This may be derived from a full shift of the ring radius which yields, the "shift of the ring" equal to the "radius of the ring." In this embodiment, the tangent of the tilt angle 46 (θ) is equal to one (i.e., shift of the ring/radius of the ring) and, thus, the tilt angle 46 (θ) is 45 degrees.

Figure 4:
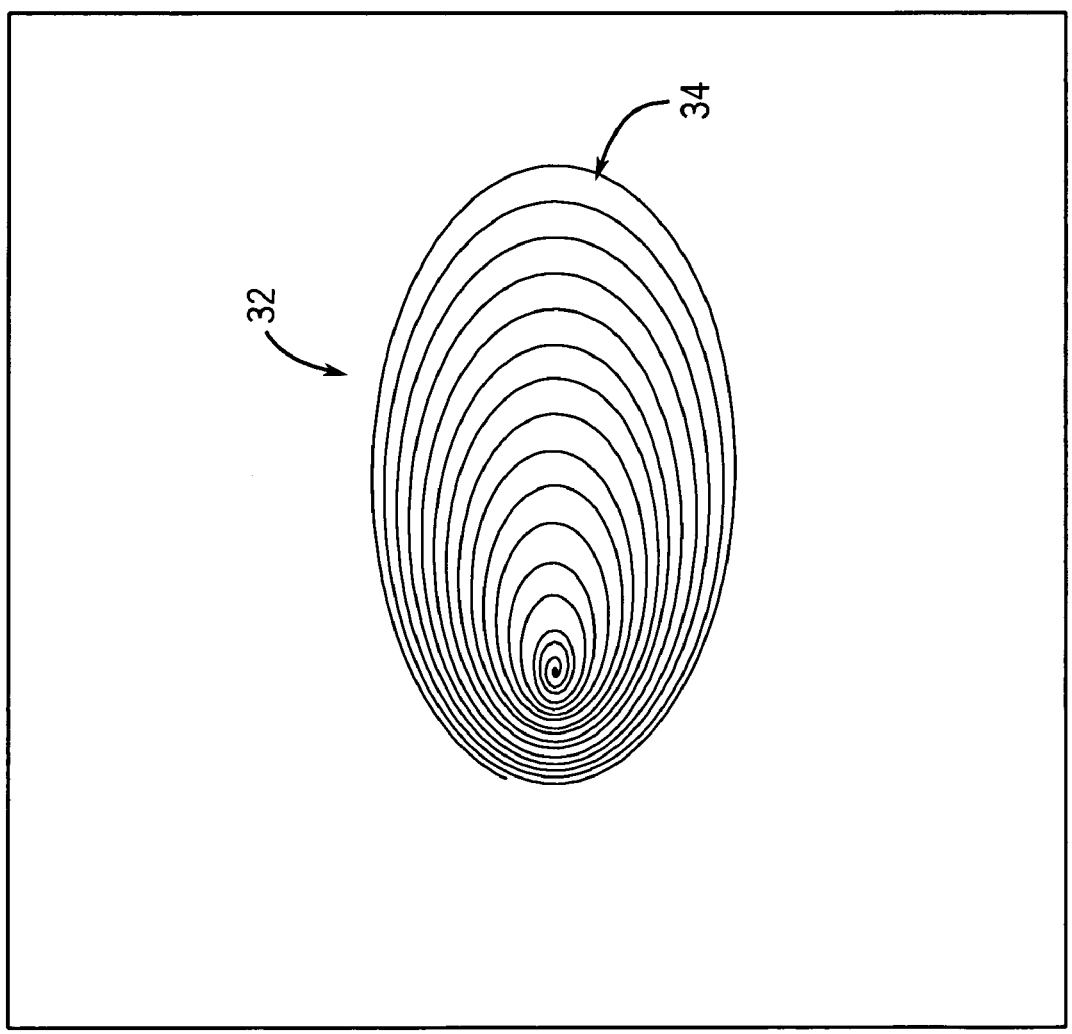
FIG. 4 is an illustration of an alternate embodiment of an exemplary planar coil in accordance with certain aspects of the present technique.

FIGS. 2 and 3 depict an embodiment wherein the planar coil 32 is formed from a spiral approximating non-concentric rings 34 that are generally circular in shape. As will be appreciated by those of ordinary skill in the art, various other shapes may be employed to provide a tilted moment vector 40. For example, as depicted in FIG. 4, the non-concentric rings 34 may take a generally elliptical shape. In addition to a generally elliptical shape, other shapes of non-concentric rings 34 may also be used that provide an appropriate distribution of current density across the planar coil 32 to provide a resulting tilted moment vector 40.

Figure 5:
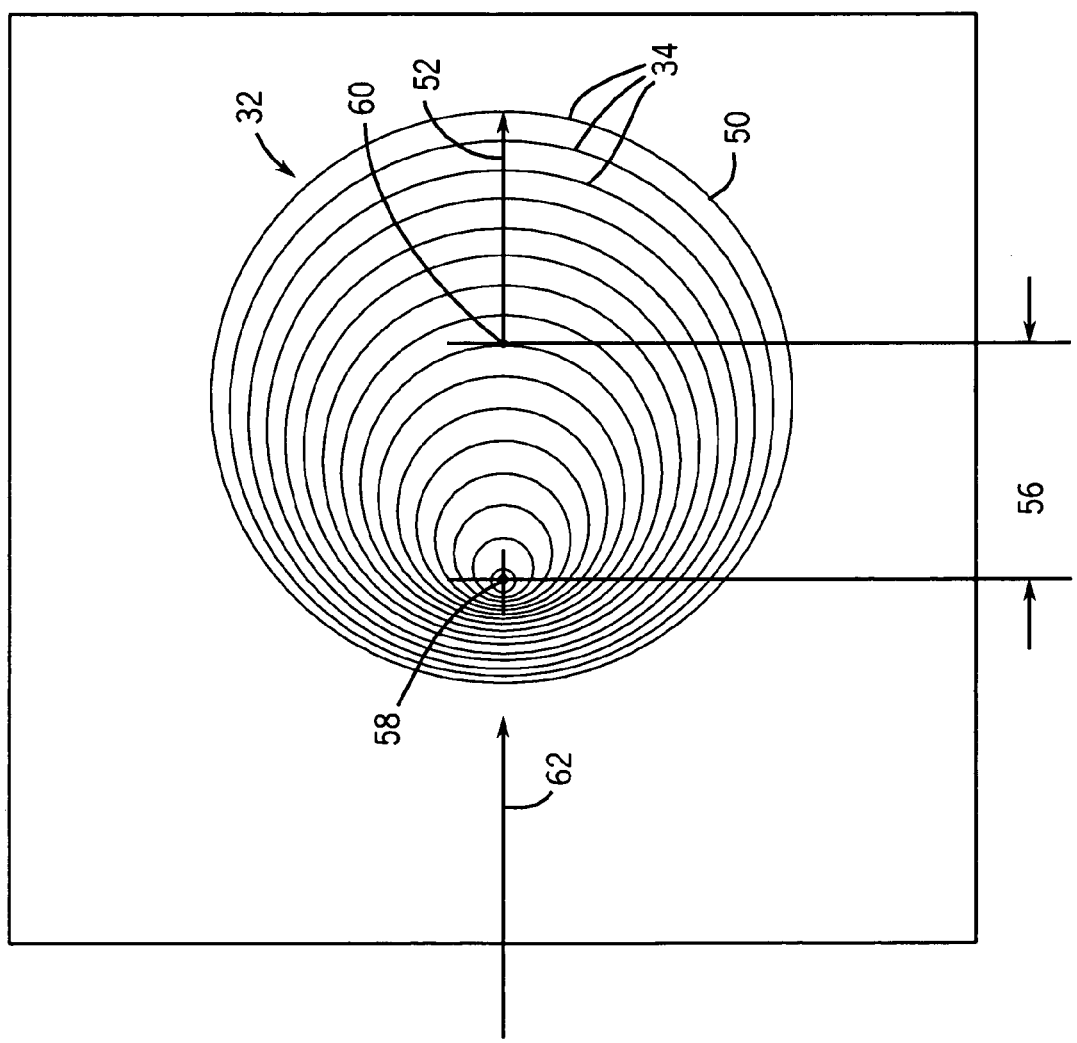
FIG. 5 is an illustration of another alternate embodiment of an exemplary planar coil in accordance with certain aspects of the present technique.

In another embodiment, the non-concentric planar coil 32 may be formed from a plurality of copper traces disposed as a plurality of non-concentric rings 34, for example, on the surface of a PCB. For example, as depicted in FIG. 5, planar coil 32 may include multiple non-concentric rings 34 formed about one another. The position and layout of the non-concentric planar coil 32 formed from multiple non-concentric rings 34 may be derived in a similar manner as the embodiment of FIGS. 2 and 3 described above. By way of example, the location of the non-concentric rings 34 of FIG. 5 may be derived by shifting each of the non-concentric rings 34, from a concentric position, in a single direction (shown by arrow 62) at a distance proportional to the radius of each respective ring 34. For example, as depicted in FIG. 5, the outer ring 50 of non-concentric planar coil 32 may have been shifted at a distance 56 (from origin 58 to the shifted center 60) that is proportional to the radius 52 of the outer ring 50. Similarly, each of the non-concentric rings 34 in the planar coil 32 may be shifted from the origin 58 in the direction 62 at a distance from the origin 58 to a shifted center, wherein the distance is proportional to the radius of each respective ring.

Figure 6:
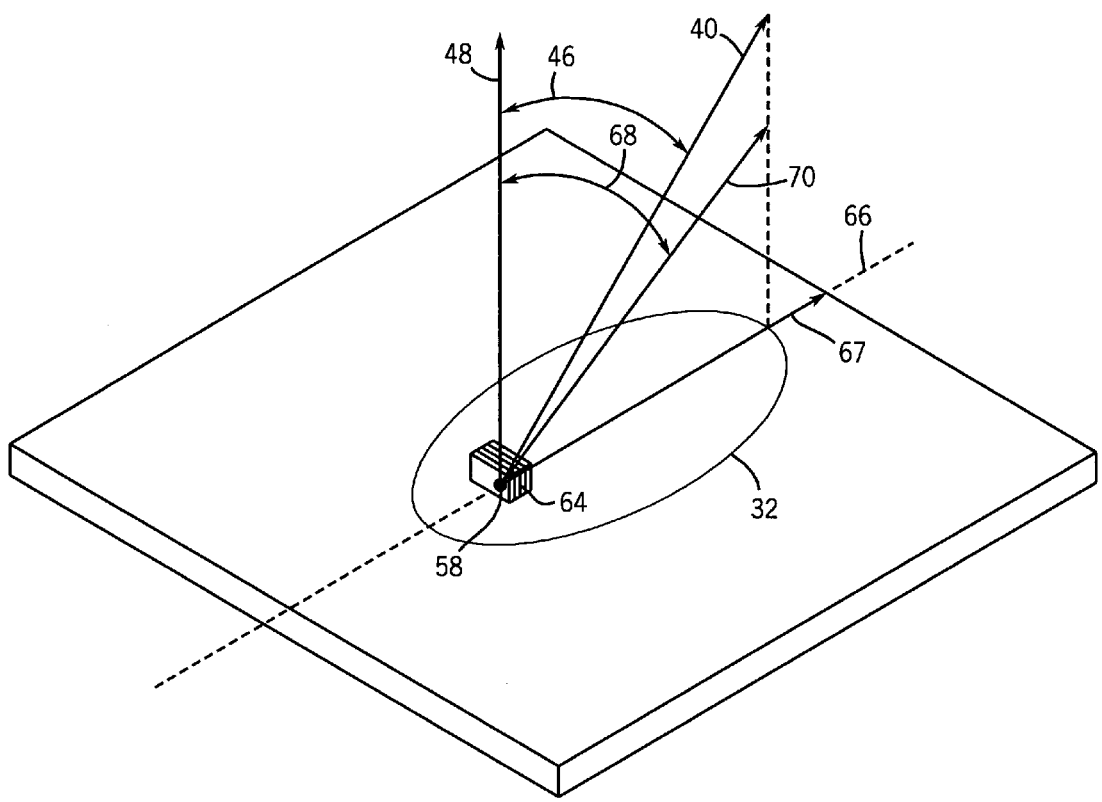
FIG. 6 is an illustration of an exemplary planar coil combined with a standard wire wound coil, and a resulting dipole moment vector in accordance with certain aspects of the present technique.

As mentioned previously, the tilt angle 46 may be limited due to the non-concentric rings 34 intersecting when shifted at a given distance 56. In one embodiment, this may be overcome by the addition of an approximate-dipole coil 64, as depicted in FIG. 6. The approximate-dipole coil 64 may have an axis 66 parallel to the shift direction 62 (see FIG. 2 and FIG. 5). As depicted in FIG. 6, an approximate-dipole coil 64 may be located at or near the origin 58. When the approximately-dipole coil 64 is energized with a drive current in coordination with a drive current to non-concentric planar coil 32, the resulting moment vector 70 may include the vector components of the tilted moment vector 40 (i.e., the moment vector 40 produced by the non-concentric planar coil 32) and the vector components of the dipole moment vector 67 (i.e., the moment vector 67 produced by the approximate dipole coil 64 along the dipole axis 66). As will be appreciated, the resulting moment vector 70 may have an increased tilt angle 68, as depicted in FIG. 6. The increased tilt angle 68 may be a function of the moment vector components of the non-concentric planar coil 32 and the approximate-dipole coil 64. The tilt angle 68 may be modified by increasing and decreasing the relative strengths of the tilted moment vector 40 and the dipole moment vector 67. For example, increasing the current through the approximately-dipole coil 64, or increasing the number of rings about the approximately-dipole coil 64 may increase the dipole moment vector 67, and thereby increase the tilt angle 68 of the resulting moment vector 70.

Figure 7:
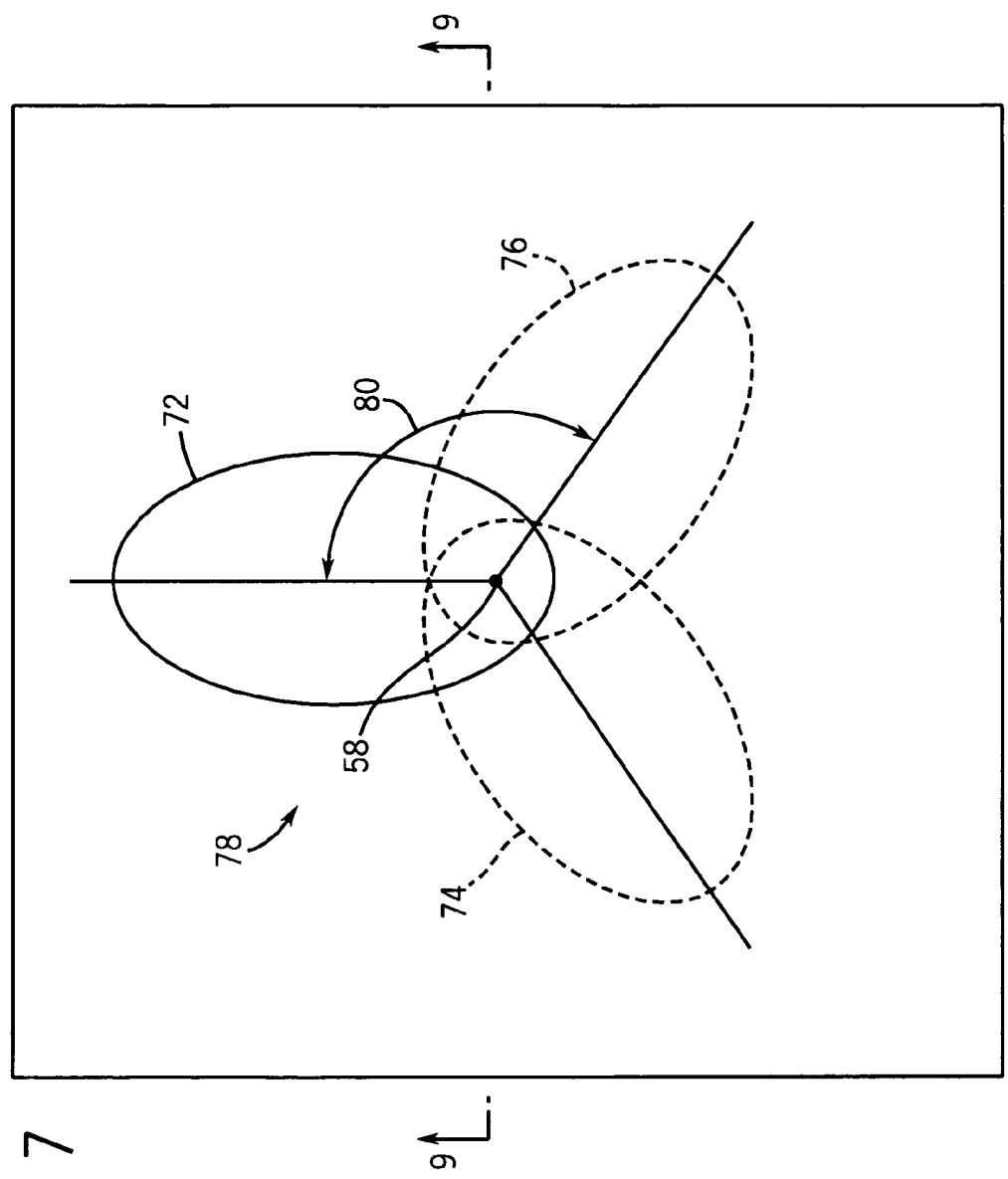
FIG. 7 is an illustration of the top view of a plurality of exemplary planar coils that are arranged to generate three generally orthogonal-dipole moment vectors in accordance with certain aspects of the present technique.
Figure 8:
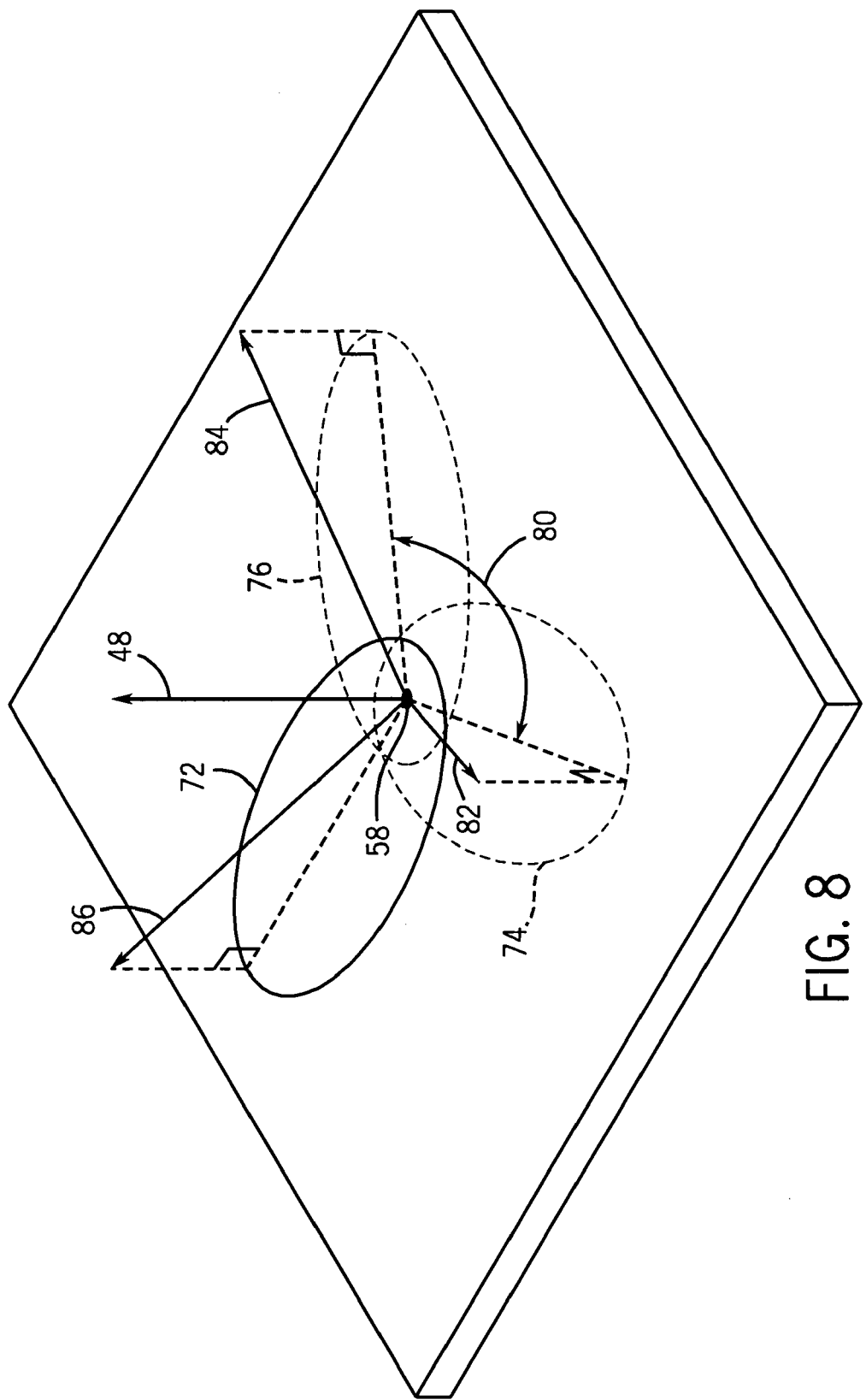
FIG. 8 is an illustration of a perspective view of a plurality of exemplary planar coils and the resulting generally orthogonal-dipole moment vectors in accordance with certain aspects of the present technique.

In addition to providing a single tilted moment vector 40, other embodiments may include a plurality of non-concentric planar coils 32 configured to provide a plurality of tilted moment vectors 46. For example, the embodiment of FIGS. 7 and 8 depict the layout of three planar coils 72, 74 and 76 that may form an approximately-orthogonal coil trio 78. In this embodiment, each of the three planar coils 72, 74 and 76 may be separated by a trio angle 80 about the origin 58. Each respective planar coil 72, 74 and 76 may generate a dipole moment vector 82, 84 and 86, as depicted in FIG. 8. In an embodiment wherein the three moment vectors 82, 84 and 86 are configured orthogonally, the trio angle 80 may be approximately 120 degrees. As will be appreciated by those of ordinary skill in the art, the number of planar coils 72, 74 and 76 may be varied, as well as varying the position, to generate a desired resulting magnetic field, or combination of magnetic fields. By providing multiple magnetic fields with varying moment vectors, tracking may be accomplished in multiple positions and orientations. For example, in one embodiment, it may be desirable to track at least dipole receiver (e.g., at least one complementary EM sensor 14 of FIG. 1) in three degrees of freedom (i.e., X, Y, Z position). To accomplish tracking in three degrees of freedom, three magnetic dipoles may be combined into a single EM sensor (such as one or more of EM sensors 12 of FIG. 1) wherein the dipole moment vectors are generally orthogonal (i.e., coil trio). The at least one complementary EM sensor 14 may then sense the individual magnetic field characteristics for processing of the three degrees of freedom. In another example, a tracking system wherein the both the EM sensors 12 and the at least one complementary EM sensor 14 are formed from coil trios (e.g., the EM sensors 12 and the at last one complementary EM sensor 14 each having three coils), the at least one EM complementary sensor 14 may be tracked in six degrees of freedom to determine position and orientation, including the X, Y and Z coordinates as wells as the roll, pitch and yaw angles.

Figure 9:
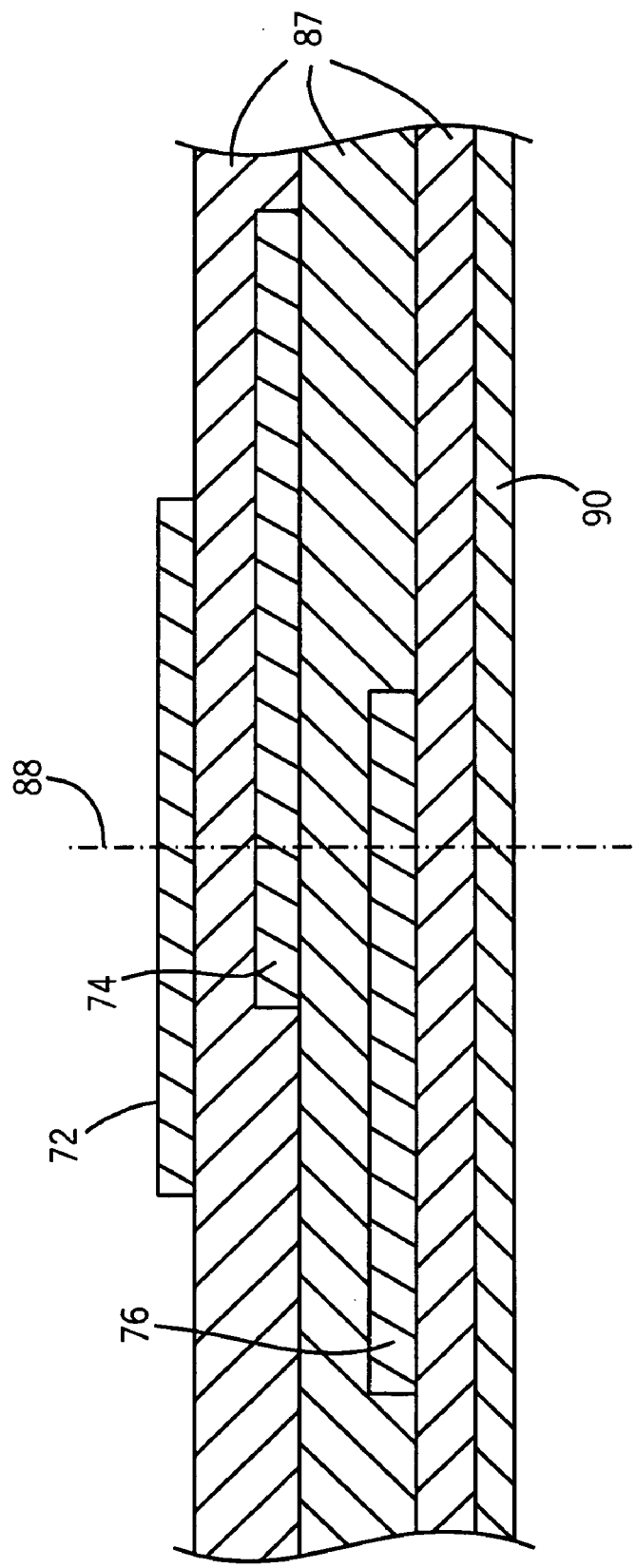
FIG. 9 is a cross sectional view of section 9-9 of FIG. 8, illustrating a multi-layer planar coil arrangement in accordance with certain aspects of the present technique.

Turning now to FIG. 9, an embodiment of a plurality of non-concentric planar coils 72, 74 and 76 is depicted in accordance with aspects of the present technique. As illustrated, an insulating layer 87 may be deposited between the each of the planar coils 72, 74 and 76. For example, FIG. 9 depicts the first second and third planar coils 72, 74 and 76 each deposited on, and electrically isolated by, three insulating layers 87. The planar coils 72, 74 and 76 may be located about a rotational axis 88 that runs orthogonal to the plane of the planar coils and through the origin 58 (see FIG. 8).

Further, an embodiment may include an electrically conductive layer 90 parallel to the plane of the insulating layers 87 and planar coils 72, 74 and 76. The electrically conductive layer 90 may prevent the magnetic field from entering the region below the electrically conductive layer 90, thereby reducing or eliminating distortions below that layer. For example, an electrically conductive layer 90 may be placed between the EM sensors 12 and a metal surgery table 24 to prevent the magnetic field from extending below the surgery table 24. As discussed previously, limiting the volume of the magnetic field may be advantageous to decrease the region wherein distorting objects (e.g., table 24 and distorting objects 30) may affect the magnetic fields generated or sensed by the EM sensors 12 and/or the at least one complementary EM sensor 14. Therefore, the addition of an electrically conductive layer 90 below the EM sensors 12 may provide for magnetic fields with moment vectors 82, 84 and 86 (see FIG. 8) that are approximately orthogonal, and not subject to distortions from the volume below the electrically conductive plane. As will be appreciated by one of ordinary skill, the depicted configuration is not limited to an arrangement of three planar coils 72, 74 and 76, but may be varied to accommodate other arrangements. For example, the number of planar coils 72, 74 and 76 may be reduced, along with the respective insulating layer 87. In another embodiment, an additional insulating layer 87 may be deposited on the first planar coil 72, and an approximately-dipole 64 coil may be coupled to the insulating layer 87. In one embodiment, the electrically conductive layer 90 may include an aluminum alloy. As will be appreciated by a person of ordinary skill in the art, the electrically conductive layer 90 may include other conductive materials.

Figure 10:
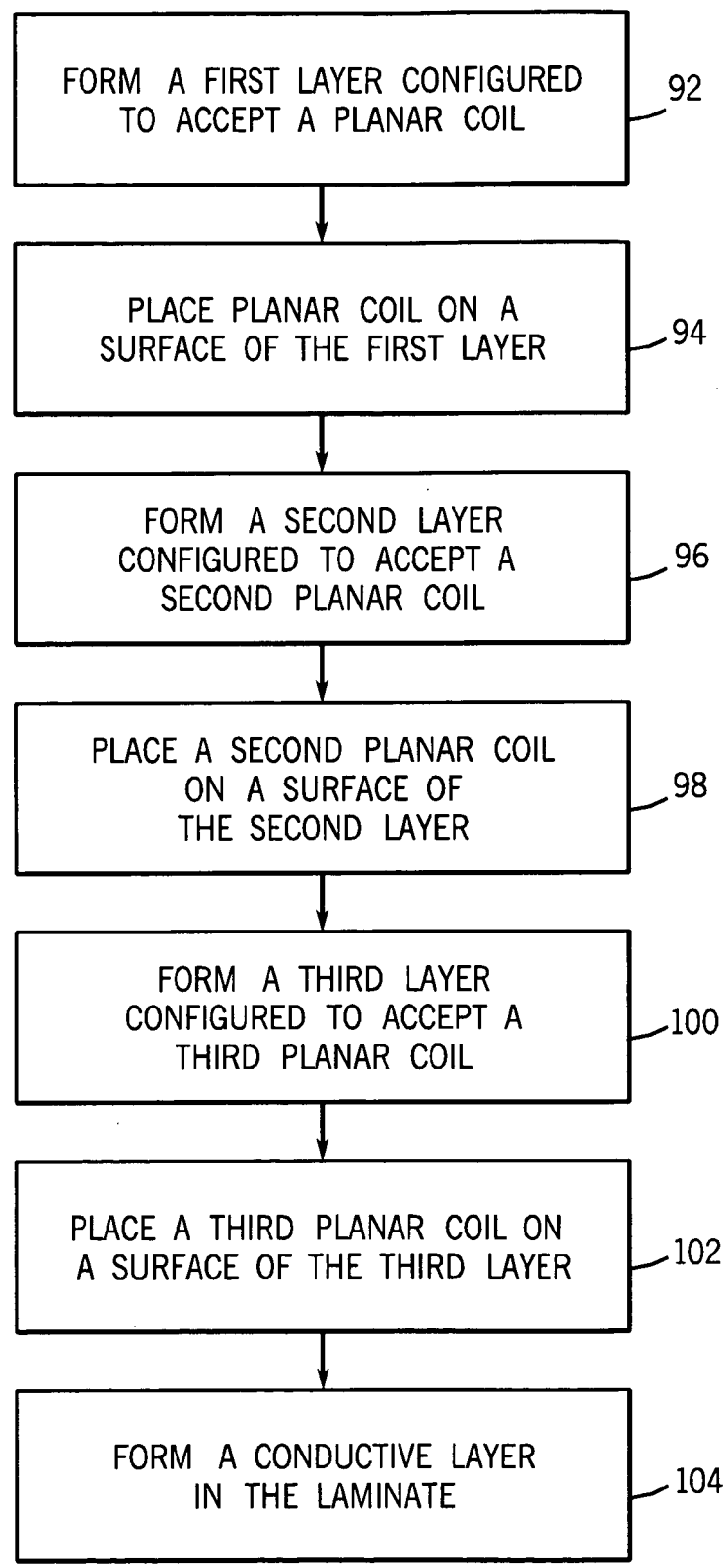
FIG. 10 is a flowchart depicting a method for manufacturing a multi-layer planar coil arrangement in accordance with certain aspects of the present technique.

FIG. 10 illustrates a method for manufacturing a plurality of non-concentric planar coils 32. For example, this embodiment may include forming the non-concentric planar coils 32 as part of a PCB laminate. At block 92, FIG. 10 includes forming a first PCB layer configured to accept a planar coil. The first layer may be formed from material configured to accept a planar coil, and configured to provide electrical insulation of a planar coil from surrounding conductive materials. Next, the method includes placing a planar coil on a surface of the first layer, as depicted at block 94. For example, a trace of conductive wire may be disposed on the surface of the first PCB layer. As depicted in block 96, the method further includes forming a second layer configured to accept a second planar coil. For example, a second PCB layer may then be deposited on top of the now formed first PCB layer and third planar coil 76. Next, the method includes placing a second planar coil on a surface of the second layer, as depicted in block 98. For example, in an embodiment of three planar coils 72, 74 and 76 each may be rotated by 120 degrees about a rotational axis 88 that runs normal or perpendicular to the planar coils and through the origin 58 (see FIGS. 7 and 8). As depicted in block 100, the method may include forming a third layer configured to accept a third planar coil. Next, block 102 depicts placing a third planar coil on a surface of the third layer. The three planar coils 72, 74 and 76 and multiple PCB layers may form a laminate. As depicted in block 104, the method further may include forming a conductive layer in the laminate. By way of example, an electrically conductive layer 90 may then be deposited on the third layer of the PCB, on the side opposite to the side where the third planar coil 76 is deposited. As will be appreciated by those of ordinary skill in the art, the method and sequence of manufacturing a plurality of planar coils 72, 74 and 76 may be varied to meet various application and manufacturing constraints. For example, the layer may be formed about the planar coils 72, 74 and 76 to combine the steps of forming the layer and depositing planar coils 72, 74 and 76 to the layer. As an additional example, the electrically conductive layer 90 may be coupled initially to the first layers, wherein the planar coils 72, 74 and 76 are subsequently coupled to the electrically conductive layer 90.

In an embodiment, the PCB is a flexible PCB made of flexible materials. For example, the PCB laminate comprising insulating layer 87, planar coils 72, 74, 76, and electrically conductive layer 90 are all made of flexible material, so that the low-profile planar sheet or flexible PCB may be rolled up for storage.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A source for inducing an electromagnetic magnetic field, comprising:
   a substrate;
   a conductive layer coupled to the substrate;
   a planar coil coupled to the substrate, wherein the planar coil comprises non-concentric rings, wherein the non-concentric rings are configured such that a drive current applied across the non-concentric rings provides a magnetic field, and wherein the magnetic field comprises a moment vector that is tilted at an angle from the normal to a plane of the planar coil; and
   a generally dipole wound coil, wherein the generally dipole wound coil is configured to modify the angle of the moment vector.

2. The source of claim 1, wherein the non-concentric rings are shifted from an origin in a direction parallel to the plane, and wherein each of the non-concentric rings are shifted in the same direction.

3. The source of claim 2, wherein the non-concentric rings are shifted a distance proportional to the radius of each respective ring.

4. The source of claim 2, wherein the dipole moment vector is tilted at an angle from the normal of the plane of the planar coil in a direction parallel to the direction of the shift.

5. The source of claim 4, wherein the angle is derived from:

Tan(θ)=(shift of ring)/(radius of ring);

wherein θ is the angle, the shift of ring is the distance from an origin of the planar coil to a shifted center of one of the non-concentric rings, and the radius of ring is the radius of the one of the non-concentric rings in the direction of shift.

6. The source of claim 1, wherein the non-concentric rings are generally circular or generally elliptical in shape.

7. The source of claim 1, comprising one or more additional planar coils.

8. The source of claim 1, comprising a second planar coil, wherein the second planar coil comprises non-concentric rings, and wherein the non-concentric rings are configured such that a drive current applied across the non-concentric rings provides a magnetic field, wherein the magnetic field comprises a moment vector that is tilted at an angle from the normal to a plane of the second planar coil, and comprising a third planar coil, wherein the third planar coil comprises non-concentric rings, and wherein the non-concentric rings are configured such that a drive current applied across the non-concentric rings provides a magnetic field, wherein the magnetic field comprises a moment vector that is tilted at an angle from the normal to a plane of the third planar coil.

9. The source of claim 8, wherein the dipole moment vectors of the planar coil, the second planar coil, and the third planar coil are generally orthogonal.

10. The source of claim 8, wherein the planar coil, the second planar coil, and the third planar coil are oriented on parallel planes, wherein an origin of each of the planar coils is generally located on a single axis, wherein the axis is normal to the particular planar coil, and wherein the planar coils are rotated approximately 120 degrees from one another about the axis.

11. The source of claim 1, wherein the source has mechanical flexibility such that the flexibility provides for the source to be rolled-up for storage.

12. A method of electromagnetic tracking, comprising:
inducing a drive current into a planar coil located on one side of an electrically conductive layer, wherein the planar coil comprises non-concentric rings, and wherein the non-concentric rings are configured such that inducing the drive current across the planar coil provides a magnetic field, wherein the magnetic field comprises a moment vector that is tilted at an angle from the normal to a plane of the planar coil; and
energizing a generally dipole wound coil, wherein energizing the generally dipole wound coil modifies the angle of the moment vector of the magnetic field.

13. The method of claim 12, wherein the electrically conductive layer is positioned between the planar coil and a distorting object, wherein the electrically conductive layer shields the magnetic field from distortions.

14. The method of claim 12, comprising sensing a magnetic field generated by the planar coil, wherein sensing the magnetic field comprises detecting at least one characteristic of the magnetic field with at least one receiver and transmitting the at least one characteristic as a signal to a processor.

15. The method of claim 14, comprising positioning at least one instrument in the magnetic field, wherein the at least one instrument is coupled to the at least one receiver.

16. The method claim 14, comprising processing the signal from the at least one receiver with the processor, wherein processing comprises determining the position and/or orientation of the at least one receiver.

17. The method of claim 12, comprising inducing a drive current into at least one additional planar coil to provide at least one magnetic field comprising a moment vector that is tilted at an angle from the normal to a plane of the additional planar coil.

18. The method of claim 17, wherein the magnetic fields provided by the planar coil and the at least one additional planar coil comprise generally orthogonal moment vectors.

19. The method of claim 17, wherein the magnetic fields generated by the planar coil and the at least one additional planar coil are distinguishable from one another by phase and frequency.

20. An electromagnetic sensor, comprising:
an insulating layer having a first surface and a second surface, the second surface being opposite the first surface;
a conductive layer coupled to the second surface of the insulating layer; and
a planar coil coupled to the first surface of the insulating layer, wherein the planar coil comprises non-concentric rings, wherein the non-concentric rings are configured such that a drive current applied across the non-concentric rings provides a magnetic field, and wherein the magnetic field comprises a moment vector that is tilted at an angle from the normal to a plane of the planar coil; and
a generally dipole wound coil coupled to the planar coil, wherein the generally dipole wound coil is configured to modify the angle of the moment vector.

21. The electromagnetic sensor of claim 20, further comprising a ferromagnetic layer coupled to the conductive layer.

22. A method of manufacture of a planar coil assembly, comprising:
coupling a planar coil to an electrically conductive layer, wherein the planar coil comprises non-concentric rings, and wherein the non-concentric rings are configured such that a inducing drive current across the planar coil provides a magnetic field, wherein the magnetic field comprises a moment vector that is tilted at an angle from the normal of a plane of the planar coil; and
coupling a generally dipole wound coil to the planar coil, wherein the generally dipole wound coil is configured to modify the angle of the moment vector.

23. The method of claim 22, comprising forming an insulating substrate about the planar coil.

24. The method of claim 22, comprising coupling a plurality of additional planar coils to the electrically conductive layer.

25. The method of claim 24, wherein an insulating substrate is provided, wherein the substrate is configured to electrically insulate the planar coils.

26. The method of claim 24, wherein coupling the plurality of planar coils comprises orienting the planar coils parallel to one another, wherein an origin of each of the planar coils is generally located on an axis, wherein the axis is normal to the plane of the planar coil, wherein the planar coils are rotated approximately 120 degrees from one another about the axis, and wherein the plurality of planar coils are configured to be electrically insulated from one another.

* * * * *